United States Patent [19]
Kiikka

[11] 4,291,180
[45] Sep. 22, 1981

[54] CO-PRODUCTION OF INDENE AND STYRENE

[75] Inventor: Oliver A. Kiikka, Willoughby, Ohio

[73] Assignee: Standard Oil Company, Cleveland, Ohio

[21] Appl. No.: 107,963

[22] Filed: Dec. 28, 1979

[51] Int. Cl.³ .................. C07C 5/42; C07C 5/367; C07C 4/12; C07C 5/48

[52] U.S. Cl. .................... 585/320; 585/361; 585/400; 585/410; 585/415; 585/422; 585/430; 585/431; 585/433; 585/443; 585/444

[58] Field of Search ............ 585/27, 319, 320, 361, 585/400, 410, 415, 422, 430, 431, 433, 443, 444

[56] References Cited

U.S. PATENT DOCUMENTS

| | | | |
|---|---|---|---|
| 2,519,577 | 8/1950 | Ipatieff et al. | 585/410 |
| 2,763,701 | 9/1956 | Hoffmann et al. | 585/400 |
| 2,984,692 | 5/1961 | Lederle | 585/400 |
| 3,183,249 | 5/1965 | Wiese | 585/360 |
| 3,502,736 | 3/1970 | Sato et al. | 585/443 |
| 3,728,406 | 4/1973 | Vrinssen et al. | 585/360 |
| 3,853,791 | 12/1974 | Feins | 208/216 PP |
| 3,887,631 | 6/1975 | Yaffe | 585/445 |
| 3,925,498 | 12/1975 | Stadig | 585/625 |
| 3,933,932 | 1/1976 | Vrieland et al. | 585/444 |
| 4,143,082 | 3/1979 | Bartek et al. | 585/437 |

OTHER PUBLICATIONS

Chem. Abs. 55, 16506b.
Chem. Abs. 74, 76220.
Chem. Abs. 75, 63494.

Primary Examiner—Curtis R. Davis
Attorney, Agent, or Firm—John E. Miller, Jr.; Herbert D. Knudsen; Larry W. Evans

[57] ABSTRACT

A process for the co-production of indene and styrene from a mixture of cyclopentadiene or dicyclopentadiene and butadiene is disclosed. The process comprises the steps of reacting cyclopentadiene or dicyclopentadiene with butadiene in a Diels-Alder reaction to form a mixture of tetrahydroindene, vinylcyclohexene and vinylnorbornene followed by the recovery of the tetrahydroindene and vinylcyclohexene, and the oxydehydrogenation of the tetrahydroindene/vinylcyclohexene mixture utilizing a composite catalyst comprising cobalt oxide and molybdenum oxide.

8 Claims, No Drawings

CO-PRODUCTION OF INDENE AND STYRENE

BACKGROUND OF THE INVENTION

This invention relates to a dehydrogenation process for producing indene and styrene, and more particularly, to a process of preparing indene and styrene from readily available butadiene and cyclopentadiene or dicyclopentadiene.

Indene is present in low concentrations (e.g., 12-16%) in ethylene or gas oil cracking co-products, but it has been difficult to recover the indene in satisfactory yields and purity from these low concentration sources. Indene is a desirable raw material for preparing superior heat-resistant polymers.

Styrene is generally produced from the catalytic dehydrogenation of ethylbenzene. For example, U.S. Pat. No. 3,933,932 describes the conversion of ethylbenzene to styrene by an oxydehydrogenation reaction utilizing catalysts such as lanthanum phosphate, lanthanum pyrophosphate or rare earth phosphates containing a major portion of lanthanum phosphates or pyrophosphates. Styrene monomer can be polymerized by exposure to light, heat or peroxide catalysts. Homopolymers and copolymers of styrene are widely used thermoplastic materials. It is, accordingly, desirable to provide additional sources of styrene from readily available materials.

Butadiene is a gas obtained from cracking of petroleum, from coal tar benzene and from acetylene. Butadiene, as well as cyclopentadiene and dicyclopentadiene, are readily available and relatively inexpensive chemicals.

The invention of this application is directed particularly to the preparation of indene and styrene from a mixture of tetrahydroindene and vinylcyclohexene. Mixtures of tetrahydroindene and vinylcyclohexene can be recovered from the reaction products formed in Diels-Alder reactions of butadiene with cyclopentadiene or its dimer, dicyclopentadiene. A considerable amount of research has been conducted and published on this reaction, and various suggestions have been made for optimizing production of the various co-products such as tetrahydroindene and vinylcyclohexene.

The dehydrogenation of indene precursers such as tetrahydroindene into indene has been described in the art and generally is conducted in the presence of dehydrogenation promoting catalysts. In U.S. Pat. No. 4,143,082, the dehydrogenation of indene precursers into indene is accomplished by contacting the indene precurser in the presence of an oxygen donor with a phosphate catalyst at elevated temperature. These catalysts, described more fully in the patent, are salts of one of the phosphoric acids. Other types of dehydrogenation catalyst have been described in the literature, and such compounds include the metal oxides, metal salts such as the halides, phosphates, sulfates, molybdates, tungstates, etc. Generally, the catalysts are characterized as compounds containing a metal having a polyoxidation state, that is, a metal having at least two oxidation states in addition to the zero state. Examples of useful polyoxidation state metals include Ti, V, Cr, Mn, Co, Ni, Cu, Nb, Mo, Ru, etc.

In addition to the use of polyoxidative state metals, oxidation catalysts also may be combined with one or more monooxidation state metals which act as promoters, initiators, stabilizers and the like. The single oxidation state metal or metal compounds include the alkali metals, and polyvalent metals such as magnesium, aluminum, calcium, scandium, zinc, etc. The use of cobalt and molybdenum oxides promoted with potassium oxide in dehydrogenating indane to indene is reported in Czech Pat. No. 135,251. The catalyst bed contained 3% CoO, 10% $MoO_3$ and 0.3% $K_2O$. A review of the various catalysts useful in oxidative dehydrogenation of organic compounds is found in U.S. Pat. No. 3,925,498. U.S. Pat. 3,887,631 describes the oxidative dehydrogenation of hydrocarbons such as butene and ethylhexane by use of a catalyst consisting essentially of the oxides of molybdenum, cobalt and boron.

SUMMARY OF THE INVENTION

It now has been found that indene and styrene can be obtained by the oxydehydrogenation of a mixture of tetrahydroindene and vinylcyclohexene, said mixture being obtained by a Diels-Alder reaction of butadiene with cyclopentadiene or dicyclopentadiene. Generally, the tetrahydroindene/vinylcyclohexene mixture is contacted with a composite catalyst comprising cobalt oxide and molybdenum oxide at temperatures of from about 300°-650° C. for a period of from about 0.1 to 30 seconds.

DESCRIPTION OF THE PREFERRED EMBODIMENTS

In accordance with the present invention, indene and styrene are co-produced from tetrahydroindene and vinylcyclohexene by oxydehydrogenation using oxygen and a composite catalyst which comprises cobalt oxide and molybdenum oxide.

In carrying out the process of the invention a mixture of tetrahydroindene and vinylcyclohexene is contacted with oxygen and a composite catalyst which comprises cobalt oxide and molybdenum oxide at an elevated temperature for a period of from about 0.1 to 30 seconds. The useful cobalt-molybdenum catalysts are commercially available from a variety of sources including the Nalco Chemical Company, Houston, Texas, and American Cyanamid Company, Bound Brook, New Jersey. These catalysts generally are contained on a support material such as carbon or alumina. U.S. Pat. No. 3,853,791 describes a variety of methods for preparing cobalt-molybdenum oxide catalysts on an alumina support. Alternatively the catalyst can be unsupported catalyst having the formula $Co_8Mo_{12}O_x$ wherein x is a number such that the valence requirements of the cobalt and molybdenum for oxygen are satisfied. This catalyst can be prepared from ammonium heptamolybdate and cobalt nitrate hexahydrate.

The catalysts which are useful in the present invention generally contain from about 1-8% cobalt and from about 8-20% of molybdenum, the percentages being by weight based on the weight of the composite and expressed as the metal oxides. The term alumina support as used in the art and in this application describes substantially pure alumina or alumina containing minor amounts, for example up to about ten weight percent, of known stabilizers such as silica. The chemical analysis of a typical commercially available cobalt-molybdenum catalyst (Nalco Sphericat 477) is as follows: $MoO_3$, 12.5%; CoO, 3.5%; $Na_2O$; 0.08%; Fe, 0.03%; $SiO_2$, 1.5%; and $Al_2O_3$, balance.

The mixture of tetrahydroindene and vinylcyclohexene is contacted in the vapor state with the oxygen and the catalyst at an elevated temperature generally from about 300° to about 650° C. and preferably from about 500° to about 650° C. The contact time can range from about 0.1 to about 30 seconds although shorter contact periods of from about 0.1 to 10 seconds are preferred. If the contact time is too long, back hydrogenation of the indene to tetrahydro and hexahydroindene is possible.

Although the cobalt-molybdenum catalysts described above are useful in the oxydehydrogenation reactions of the invention, it has been found that improved results are obtained when the promoters for the catalysts are included. It appears that the presence of the promoter reduces the extent of catalyst fouling caused at least in part by the formation of carbon deposits on the catalyst during the dehydrogenation reaction.

Alkali metal compounds can be included with the catalyst in limited quantities as a promoter for the catalytic reaction. Examples of particularly useful promoters include potassium oxide, cesium oxide and rubidium oxide. Although the optimum type and quantity of promoter may vary depending upon the reaction conditions and the reactants, the use of potassium oxide in quantities of up to 28% or more generally is preferred.

The size of the catalyst particles is not critical and can vary between wide limits. For example, the catalyst particle size may be extremely small (e.g., microspheroidal) so that the catalyst can be employed in a fluid-bed reactor or the catalyst can be significantly larger in particle size so that the catalyst can be employed in a fixed-bed reactor.

As an oxygen donor, elemental oxygen, $O_2$ generally is employed. In particular, air is normally employed as a feed since it is the cheapest and the most convenient oxygen donor or source. Other compounds which will serve as oxygen donors and dehydrogenation reactions can be employed such as, for example, $SO_2$, COS and HOCl.

The amount of oxygen fed to the reaction vessels should be at least the stoichiometric amount necessary to react with all of the hydrogen to be withdrawn from the feed. Of course, less than stoichiometric amounts can be fed to the reactor, but this can decrease the efficiency of the process. Preferably, the amount of oxygen donor fed to the reaction vessel is at least twice, preferably two to five times, the stoichiometric amount necessary to react all of the hydrogen withdrawn from the feed.

In addition to the foregoing components, a gaseous promoter known to increase oxidation rates also can be fed to the reaction vessel for improving the efficiency of the dehydrogenation reaction. For example, certain compounds such as halides (gaseous HCl, HBr, $Cl_2$, $Br_2$ and alkyl halides containing one to five carbon atoms) promote various types of dehydrogenation reactions. In accordance with the present invention, the gaseous promoters are fed to the reaction vessel generally along with the oxygen donor for increasing the efficiency of the dehydrogenation reaction. When a gaseous promoter is employed, it is preferable that the amount be less than 10%.

The materials fed to the reaction vessels also can contain a gaseous diluent. Any gas inert to the reaction and catalyst can be employed as the diluent. Preferred diluents are $N_2$, $CO_2$, $H_2O$, combustion gases and light hydrocarbon gases (for example, methane). When the oxygen donor is $O_2$, the amount of inert diluent should be from 0 to 20 times the amount of $O_2$ fed to the reaction vessel. When other oxygen donors are employed, a stoichiometrically corresponding amount of inert diluent can be employed. The dehydrogenation reactions can be carried out either in a fixed-bed or fluid-bed reactors. In fixed-bed reactors, the liquid hourly space velocity of the feed is from 0.01 to 10 and preferably from 0.05 to 1 hour$^{-1}$. The contact time generally is from about 0.1 to 30 seconds and preferably from 0.1 to 10 seconds. The reaction pressure is normally maintained at approximately atmospheric pressure, although lower or higher pressures can be employed if desired.

The efficacy of the method of the invention for producing indene and styrene is illustrated in the following examples which are conducted in a 20 cc. fixed bed reactor. The general procedure is as follows. Nitrogen is bubbled through a saturator containing the tetrahydroindene, vinylcyclohexene and water. This mixed feed, along with combustion air, enters the reactor. Both nitrogen and air are fed through calibrated rotameters. The rates, including product of gas, are measured by timing bubble travel in a 50 cc. burette. The feed rate is determined by weighing the saturator before and after a series of runs knowing the on-stream time. The residual feed is split into a hydrocarbon-water fraction to determine the actual amounts of each feed.

The reactor effluent is collected in two knock-out flasks connected in series and mounted in an ice bath. The second flask contains distilled water. Most of the liquid product recovered generally is condensed in the first flask (90+%). This product is analyzed gas gas chromatography and no solvents or dilution is used. The retention times are confirmed either by spiking the liquid product or running separately high purity knowns. The reactor back pressure normally is about 0.1 PSIG. Therefore 0.5 mm was added to the atmospheric pressure in calculating the amount of air, off gas ratio and contact time. The data reported in the table are on an uncorrected carbon balance because the relative amount of deposits formed in the catalyst is unknown for each run. The percent conversion and percent selectivity are defined from their respective feed and liquid product analyses.

The catalyst used in this example of the invention is Sphericat 477, a cobalt molybdenum catalyst available from Nalco Chemical Company analyzing, on a dry basis, 12.5% $MoO_3$, 3.5% CoO, 0.08% $Na_2O$, 0.03% Fe, 1.5% $SiO_2$ and the balance $Al_2O_3$. The catalyst is promoted with 1% $K_2O$. The hydrocarbon feed is a blend of 7.6 parts of vinylcyclohexene and 3.1 parts of tetrahydroindene. The ratio of hydrocarbon/$H_2O$/Air/$N_2$ is 1/2.5/4.5/7.5, and the contact time is about 0.75 sec. The temperature of the reactor is 515° C. Two samples of reactor effluent are collected and analyzed, one during the first half hour (sample 1) and one during the second half hour (sample 2). The results of the analysis are summarized in the following Table.

|  | Sample | |
| --- | --- | --- |
|  | 1 | 2 |
| Conversion (%) | 98.1 | 93.8 |
| Indene (%) | 14.05 | 20.15 |
| Indane (%) | 0.89 | 2.10 |
| Indene/Indane | 15.8 | 9.6 |
| Styrene (%) | 37.60 | 34.36 |
| Ethyl Benzene (%) | 44.18 | 33.71 |

The above results demonstrate the feasibility of producing indene and styrene from a mixed feed of vinylcyclohexene and tetrahydroindene. The high indene:indane ratio especially is significant since ratios of these magnitudes generally are difficult to obtain from the dehydrogenation of other indene precursors. Moreover the mixture of styrene and indene is desirable for production of copolymers and terpolymers having desirable properties.

I claim:

1. A process for co-production of indene and styrene from a mixture of cyclopentadiene or dicyclopentadiene and butadiene which comprises the steps of
   (a) reacting cyclopentadiene, dicyclopentadiene or mixtures thereof with butadiene at an elevated temperature pressure to form a mixture comprising tetrahydroindene, vinylcyclohexene and vinylnorbornene,
   (b) recovering the tetrahydroindene and vinylcyclohexene,
   (c) contacting the mixture of tetrahydroindene and vinylcyclohexene with an oxygen donor and a catalyst comprising cobalt oxide and molybdenum oxide at a temperature above about 300° C. for a period of from 0.1 to 30 seconds, and
   (d) recovering a mixture of indene and styrene.

2. The process of claim 1 wherein the reaction in step (a) is conducted at a temperature of from about 150° to 250° C. at a pressure of up to about 800 PSIG.

3. The process of claim 1 wherein the reaction in step (c) is conducted at a temperature of from about 300° to 650° C.

4. The process of claim 1 wherein the catalyst is promoted with an alkali metal oxide.

5. The process of claim 4 wherein the catalyst is promoted with 0.5 to 2% potassium oxide, cesium oxide or rubidium oxide.

6. The process of claim 1 wherein the catalyst comprises from about 1 to 8% of cobalt oxide and 8 to 20% of molybdenum oxide on a support.

7. The process of claim 1 wherein the catalyst comprises from about 1 to 8% of cobalt oxide, about 8 to 20% of molybdenum oxide, and 1 to 2% of silica supported on alumina.

8. The process of claim 1 wherein the oxygen donor is air.

* * * * *